(12) United States Patent
Mizuochi

(10) Patent No.: US 8,061,840 B2
(45) Date of Patent: Nov. 22, 2011

(54) OCULAR LIGHT STIMULUS APPARATUS

(75) Inventor: Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 12/798,544

(22) Filed: Apr. 6, 2010

(65) Prior Publication Data

US 2010/0253910 A1    Oct. 7, 2010

(30) Foreign Application Priority Data

Apr. 7, 2009    (JP) .................. 2009-092604

(51) Int. Cl.
*A61B 3/14* (2006.01)
(52) U.S. Cl. ...................... 351/206; 351/211
(58) Field of Classification Search .......... 351/206, 351/205, 221, 211, 212, 214, 216
See application file for complete search history.

(56) References Cited

U.S. PATENT DOCUMENTS 7,815,312 B2 * 10/2010 Matsumura et al. .......... 351/216
2009/0231543 A1 * 9/2009 Hara et al. .................. 351/206

* cited by examiner

*Primary Examiner* — Hung Dang
(74) *Attorney, Agent, or Firm* — Adams & Wilks

(57) ABSTRACT

An ocular light stimulus apparatus provides the ocular fundus of an examinee's eye under examination with observation light to observe the ocular fundus and provides localized background light and stimulus light to a retina of the ocular fundus to perform biological examination through use of a bioelectrical signal from the retina. The ocular light stimulus apparatus has a ring slit and a photographic stop. Each of the ring slit and the photographic stop is disposed in a position substantially conjugate with the anterior ocular segment of the eye to be examined so that the ocular fundus of the eye is irradiated with the ocular fundus observation light via the ring slit and is irradiated with the stimulus light and the background light via the photographic stop.

15 Claims, 8 Drawing Sheets

OCULAR LIGHT STIMULUS APPARATUS

BACKGROUND OF THE INVENTION

1. Field of the Invention

The present invention relates to an ocular light stimulus apparatus, and more particularly relates to an ocular light stimulus apparatus in which the ocular fundus of an examinee's eye is irradiated with ocular fundus observation light to observe the ocular fundus and is irradiated with background light and stimulus light to locally stimulate the retina with the stimulus light and perform a biological examination using a bioelectrical signal obtained from the retina.

2. Description of the Prior Art

Conventional known methods used primarily for ophthalmological examination include not only capturing a fundus image and performing fundus examination, but also electroretinogram (ERG) examination in which stimulus light is projected onto a retina to measure an action potential generated in the retina, and an electroretinogram is created to perform an ophthalmological biological examination.

In an ERG examination, the ocular fundus is irradiated with visible stimulus light, and the background irradiated with the stimulus light has to be illuminated by background light. A suitable combination of the intensity of the background light and the intensity of the stimulus light affects the quality of the ERG examination. When the stimulus light is projected locally (local ERG) on a macular spot of the ocular fundus to perform the ERG examination, the background light is projected as visible light onto the ocular fundus.

The background light is projected, e.g., from between an objective lens and an apertured mirror onto the ocular fundus via a half mirror (Journal of Japanese Ophthalmological Society, Vol. 85 (10) (Oct. 10, 1981, 9-(1521) to 19-(1531)).

According to the configuration disclosed in Japanese Laid-open Patent Application No. 2006-42952, the ocular fundus is irradiated with white light using a white light-emitting diode arranged in the observation optical system, and, with this as a background, a spot light is projected as stimulus light from a high-luminance light-emitting diode to perform a local ERG examination while the ocular fundus is observed using infrared light.

According to the configuration of WO2008/111166A1, a working distance light source may also be used as a background light source for a local ERG examination, and the visible light from the light source is projected as the background light onto the ocular fundus.

However, with a conventional local ERG examination, background light is projected from an illumination optical system or by using the effective outside diameter of a photographic stop. Therefore, the amount of background light directed onto the ocular fundus is varied by the pupil diameter of the eye to be examined, causing measurement error and making it difficult to perform an accurate local ERG examination.

SUMMARY OF THE INVENTION

It is therefore an object of the invention to provide an ocular light stimulus apparatus that can perform a reliable biological examination.

The present invention is an ocular light stimulus apparatus in which the ocular fundus of an examinee's eye is irradiated with ocular fundus observation light to observe the ocular fundus and is irradiated with background light and stimulus light to locally stimulate the retina with the stimulus light and perform a biological examination using a bioelectrical signal obtained from the retina. The ocular light stimulus apparatus comprises a ring slit disposed in a position substantially conjugate with the anterior ocular segment of the eye to be examined, and a photographic stop disposed in a position substantially conjugate with the anterior ocular segment of the eye to be examined. The ocular fundus of the eye to be examined is irradiated with the ocular fundus observation light via the ring slit, and the ocular fundus of the eye to be examined is irradiated with the stimulus light and the background light via the photographic stop.

With such an arrangement, the background light is projected onto the ocular fundus of the eye to be examined via a photographic stop that is disposed in the position conjugate with the anterior ocular segment of the examinee's eye. Therefore, the background light is projected onto the ocular fundus in such a manner that it spreads to the four corners about the center of the anterior ocular segment, and the entire ocular fundus can be uniformly illuminated by the background light about the position onto which the stimulus light is projected. This allows the effect of scattered light due to the stimulus light to be canceled out and an accurate local ERG examination to be performed.

The ocular fundus is irradiated with ocular fundus observation light via a ring slit disposed in a position conjugate with the ocular fundus of the eye to be examined. When the pupil diameter of the eye to be examined is small, the ocular fundus observation light undergoes shading and the amount of illumination light varies because the ocular fundus observation light is projected onto the ocular fundus from the periphery of the pupil. However, the ocular fundus observation light is infrared light, and the ERG measurement is not affected in any way. On the other hand, the ocular fundus is irradiated with the background light and the stimulus light via the central part of the pupil. Therefore, even when the pupil diameter is somewhat smaller, the shading does not occur and the amount of the background light and the stimulus light can be kept constant regardless of the pupil diameter, and a highly reliable local ERG examination can be carried out.

Further features of the invention, its nature and various advantages will be more apparent from the accompanying drawings and following detailed description of the invention.

DESCRIPTION OF THE PREFERRED EMBODIMENTS

Figure 1:
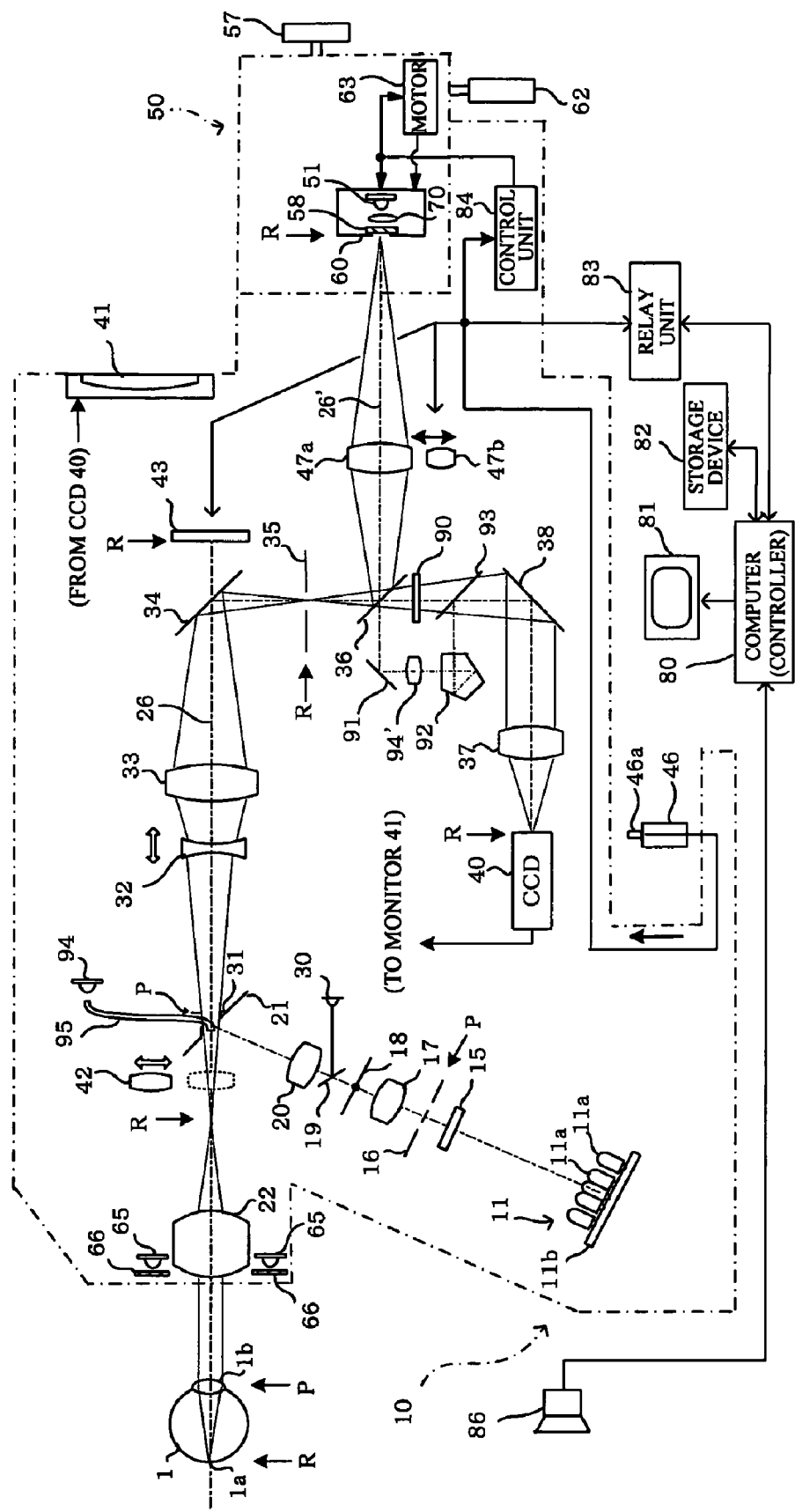
FIG. 1 is a schematic view showing the overall configuration of an ocular light stimulus apparatus according to a first embodiment of the present invention.

The present invention will be described in detail hereinafter with reference to the embodiments shown in the drawings.

FIG. 1 shows a first embodiment of an ophthalmological examination apparatus configured as a light stimulus apparatus comprising a light stimulus main unit 10 and a stimulus light source unit 50. In FIG. 1, R is the position conjugate with the ocular fundus 1a of the eye 1 to be examined, and P is the position conjugate with the anterior ocular segment 1b (particularly the pupil) thereof.

Figure 2:
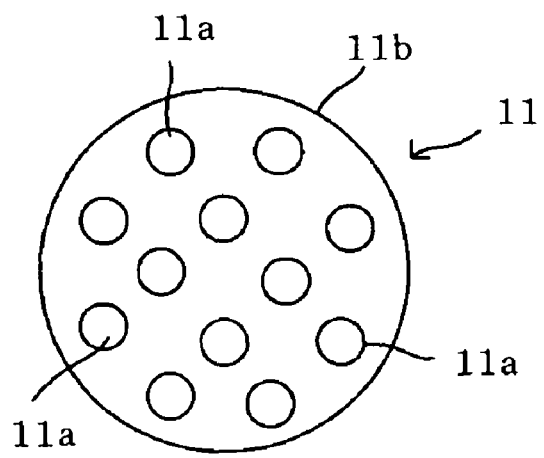
FIG. 2 is an illustrative view showing the arrangement of an illumination light source for illuminating the ocular fundus.

The light stimulus main unit 10 is provided with an illumination optical system for illuminating the ocular fundus of the eye to be examined and an observation/projection optical system for observing the illuminated ocular fundus and projecting stimulus light and background light. An illumination light source 11 is disposed in the illumination optical system, and is composed of a plurality of LEDs (light-emitting diodes) 11a that are arranged on a substrate 11b so as to emit infrared light, as shown in FIG. 2.

The infrared light from the illumination light source 11 is incident on and diffused by a diffusion plate 15, and illuminates a ring slit 16 disposed in a position P conjugate with the anterior ocular segment (pupil) 1b of the eye 1 to be examined. The illumination light from the ring slit 16 passes through a lens 17, a black spot plate 18 for eliminating reflection from an objective lens 22, a half mirror 19, and a relay lens 20, and is reflected by an apertured full reflection mirror 21 having an aperture in the center. The illumination light then passes through the objective lens 22, and is incident on the ocular fundus 1a to illuminate it by way of the anterior ocular segment 1b of the eye 1 to be examined.

The light reflected from the ocular fundus 1a is received via the objective lens 22, and passes through the aperture of the full reflection mirror 21, a photographic stop (aperture stop) 31 disposed in the position P conjugate with the anterior ocular segment, a focus lens 32, and an imaging lens 33. The light that has passed through the imaging lens 33 is then reflected by a half mirror 34 and is incident on a half mirror 36 via a field stop 35 disposed in the position R conjugate with the ocular fundus. The infrared light that has passed through the half mirror 36 is reflected by a mirror 38, passes through an imaging lens 37, and is incident on an image-capturing device 40 that is disposed in the position R conjugate with the ocular fundus and that is composed of an infrared CCD sensitive to infrared light and visible light regions. The signal from the image-capturing device 40 is inputted to a monitor 41.

The photographic stop 31, the focus lens 32, the imaging lens 33, the field stop 35, and the like following the objective lens 22 constitute an observation/projection optical system.

The stimulus light source unit 50, which houses a stimulus light source 51 composed of a light-emitting diode or the like for emitting visible light, is mounted on the light stimulus main unit 10. The stimulus light source 51 can be moved within the xy plane vertical to the projection optical axis 26' using a lever 57.

The stimulus light source unit 50 is provided with an indicator disc 60 which has a plurality of apertures with mutually different diameters and which is rotatably arranged in the ocular fundus conjugate position R. To vary the spot diameter of the stimulus light, a lever 62 or a motor 63 is used to rotate the indicator disc 60 to a position in which any of the apertures is positioned facing the stimulus light source 51 and a diffusion plate 58.

The stimulus light source 51 is turned on by a control unit 84 when a switch 46a provided to a joystick 46 is operated. Light from the stimulus light source 51 is projected onto and diffused by the diffusion plate 58 via a lens 70, and is set to a predetermined spot size by the selected aperture of the indicator disc 60. The visible light from the stimulus light source 51 that has passed through a magnification lens 47a (47b) is divided and reflected by the half mirror 36, and is projected as stimulus light onto the ocular fundus 1a from the pupil 1b of the eye to be examined via the mirror 34, the lenses 33, 32, the photographic stop 31, the aperture of the apertured full reflection mirror 21, the objective lens 22, and the like.

In addition to the stimulus light, the background light, which is visible light, is projected onto the ocular fundus 1a in the ERB examination. A liquid crystal (LCD) plate 43 is used as a light source for the background light, and is disposed behind the half mirror 34 so that the center thereof is in coincidence with the optical axis 26 of the projection optical system.

Figure 3:
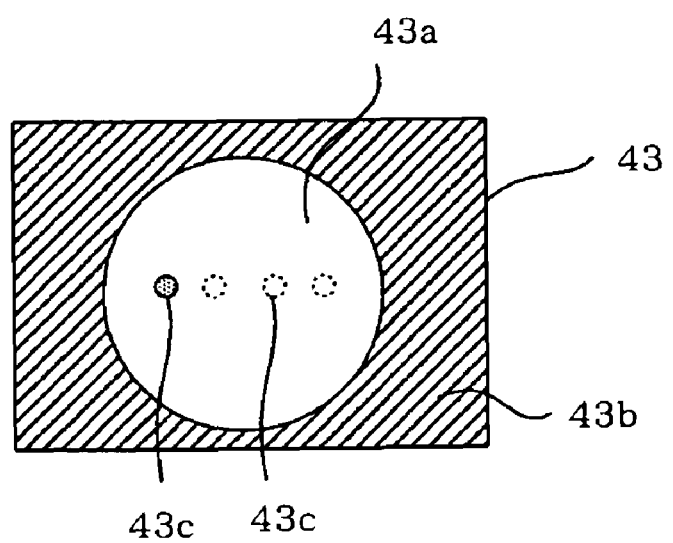
FIG. 3 is an illustrative view showing a liquid crystal panel used as a background light source.

The liquid crystal plate 43 is composed of a circular liquid crystal panel 43a arranged in the center of opaque rectangular plate 43b, as shown in FIG. 3, and, when powered, the liquid crystal panel 43a emits a weak white light (visible light). The background light from the liquid crystal panel 43a is projected onto the ocular fundus 1a via the half mirror 34, the imaging lens 33, the focus lens 32, the photographic stop 31, and the objective lens 22. The center of the liquid crystal panel 43a and the center of the photographic stop 31 are arranged so as to align with the optical axis 26, and the photographic stop 31 is disposed in the position P conjugate with the anterior ocular segment. Therefore, when the eye 1 to be examined is aligned, as shown in FIG. 1, the background light from the liquid crystal panel 43a is projected via the center of the anterior ocular segment (pupil) 1b radially onto the ocular fundus 1a.

A plurality (four, in FIG. 3) of fixation markers 43c composed of liquid crystal are displayed inside the liquid crystal panel 43a in order to allow the liquid crystal plate 43 to serve as an internal fixation lamp. The fixation marker 43c is varied from white to non-white color, e.g., black spot, when a predetermined voltage is applied, and the examiner can reliably carry out alignment and focusing operations by having the examinee gaze at the fixation marker 43c which has changed into the black spot.

An ERG electrode 86 is mounted on the eye 1 to be examined, and a signal from the electrode 86 is inputted to a computer (personal computer) 80 provided with a display 81 and a storage device 82. An electroretinogram is created in the computer 80, displayed on the display device 81, and stored in the storage device 82.

The visible stimulus light that has been divided and transmitted by the half mirror 36 is reflected by the mirror 38 via a mirror 91, a lens 94', a prism 92, and an infrared-transmitting visible light-reflecting mirror 93, and enters the image-capturing device 40 so that the position of the stimulus light source 51 and/or size of the projection index (stimulus light) by the stimulus light source 51 can be displayed on the monitor 41.

The visible light from the stimulus light source 51 that is divided and reflected by the half mirror 36 is reflected by the surface of the imaging lens 33 and returned as reflected light.

In order to prevent the reflected visible light from entering the image-capturing device 40, a filter 90 for transmitting infrared light and reflecting visible light is inserted between the half mirror 36 and the infrared-transmitting visible light-reflecting mirror 93. In this case, the infrared ocular fundus observation light enters the image-capturing device 40 without being blocked by the filter 90 because the filter 90 has infrared-transmitting properties.

A working distance light source 94 (hereinafter referred to as WD light source) is provided for alignment. The WD light source 94 is composed of an infrared light-emitting diode, and the light beam thereof is directed via an optical fiber 95 to the aperture center of the apertured full reflection mirror 21 to form a working distance marker. The working distance marker is projected by the objective lens 22 onto the cornea of the eye 1 to be examined, and the working distance is adjusted so that the light beam specularly reflected by the cornea of the eye 1 is substantially afocal.

A focus dot light source 30 (hereinafter referred to as FD light source) composed of an infrared light-emitting diode is provided to the illumination optical system. Infrared light from the light source 30 is incident on the ocular fundus 1a via the half mirror 19, and the focus dot position is varied in accordance with the movement of the focus lens 32. Therefore, the examiner can adjust the focus on the eye to be examined by observing the focus dot.

In the initial alignment step, an anterior ocular segment observation lens 42 is inserted in the side of the objective lens 22 opposite to the eye to be examined, and the anterior ocular segment 1b is illuminated by infrared light that comes from an anterior ocular segment illumination light source 65 and that is diffused by a diffusion plate 66. The examiner can confirm the image of the anterior ocular segment 1b using the monitor 41 and perform alignment on the basis of the image of the anterior ocular segment. The fixation markers 43c described above are turned on during alignment and focus operations, and the examiner can reliably perform alignment and focus operations by having the examinee gaze at the fixation lamp.

A computer (controller) 80 can set various measurement conditions in order to perform a local ERG examination. The measurement conditions include background light intensity (amount of light) obtained from the liquid crystal plate 43, stimulus light intensity (amount of light) from the stimulus light source 51, the wavelength component of the background light and the stimulus light, the spot diameter of the stimulus light (aperture position of the indicator disc 60), the irradiation time (lighting time) of the stimulus light, the number of irradiation cycles of the stimulus light, the on-off interval of the stimulus light, the position of the fixation marker (which fixation markers 43c is turned on), and the on-off state of the various light sources 11, 65, 30, 94, 43.

A hardware configuration may be used so that the control carried out by the computer 80 is entirely carried out by the control unit 84 in the main unit 10. Conversely, the system may also be configured so that the control carried out by the control unit 84 in the main unit is entirely carried out by the computer 80 outside the main unit 10. The assignment of these roles are design details that can be established as needed.

In the present embodiment, a relay unit 83 is provided for relay between the light stimulus apparatus and the computer 80, and for synchronizing retina stimulation with measurement conditions set in the computer 80. The relay unit 83 may be provided inside the light stimulus apparatus, or may double as the computer 80.

A local ERG examination will be performed as follows using the ocular stimulus apparatus as described above.

First, one of the fixation markers 43c of the liquid crystal plate 43 is turned on and the examinee gazes at the fixation marker. The anterior ocular segment illumination light source 65 is turned on to illuminate the anterior ocular segment 1b of the eye 1 with infrared light, and the examiner observes the image of the anterior ocular segment on the monitor 41 and carries out anterior ocular segment alignment.

Next, the anterior ocular segment observation lens 42 is removed from the optical path, and the anterior ocular segment illumination light source 65 is turned off. The LED's 11a of the illumination light source 11 are then turned on to irradiate the ocular fundus 1a with infrared light. The WD light source 94 and the FD light source 30 are further turned on, and the examiner performs the ocular fundus alignment and focus operations while observing the ocular fundus image on the monitor 41.

The biological examination is started when the ocular fundus alignment and focusing are completed. In the biological examination, the liquid crystal panel 43a is turned on, and the background light from the liquid crystal panel 43a is projected from the anterior ocular segment (pupil) 1b onto the ocular fundus 1a via the photographic stop 31. The stimulus light source 51 is also turned on, and the stimulus light from the stimulus light source 51 is similarly projected from the anterior ocular segment 1b onto the ocular fundus 1a via the photographic stop 31. The retina of the eye illuminated by the background light is thus locally stimulated by the stimulus light, and a bioelectrical signal is generated from the retina.

The stimulus light from the stimulus light source 51 can be varied in position in the xy plane vertical to the projection optical axis 26', as described above, and the spot size of the stimulus light can be changed by the indicator disc 60. The amount of stimulus light and the amount of background light are adjusted by a rotary switch or the like provided to the controller 80. The FD light source 30 is turned off during the biological examination because the light of the focus dot interferes with the monitor. The other light sources 11, 94 and the fixation markers 43c are left on.

The bioelectric signal from the ERG electrode 86 is inputted to the computer 80, and an electroretinogram is created, displayed on the display device 81, and stored in the storage device 82.

In a local ERG examination, the background light acts to cancel the effect of the scattered stimulus light and the ocular fundus is therefore to be illuminated in a uniform fashion in a wider range about the center of the projected stimulus light, i.e., the entire visual range of the ocular fundus. In the embodiment described above, the background light is incident on the anterior ocular segment 1b via the photographic stop 31 disposed in a position conjugate with the anterior ocular segment 1b of the examinee's eye, and is projected onto the ocular fundus so as to spread in all directions about the center Of the anterior ocular segment (pupil) 1b. This allows the background light to be projected to a wide range about the position in which the stimulus light is projected. Therefore, the entire ocular fundus can be uniformly illuminated, the effect of scattered light by the stimulus light is canceled out, and an accurate local ERG examination can be performed.

The ocular fundus illumination light (ocular fundus observation light) from the illumination light source 11 is projected from the periphery of the pupil to the ocular fundus via the ring slit 16 that is disposed in a position conjugate with the anterior ocular segment 1b of the eye to be examined. Therefore, the ocular fundus illumination light undergoes shading (eclipse) and the amount of illumination light varies when the pupil diameter of the eye to be examined is small. However, since the ocular fundus illumination light is infrared light, the ERG measurement is not affected in any way. On the other hand, the background light and the stimulus light are projected onto the ocular fundus via the central part of the pupil, so that the shading does not occur even when the pupil diameter is somewhat smaller. The amount of the background light and the stimulus light can be kept constant regardless of the pupil diameter, and a highly reliable local ERG examination can be carried out.

Figure 4:
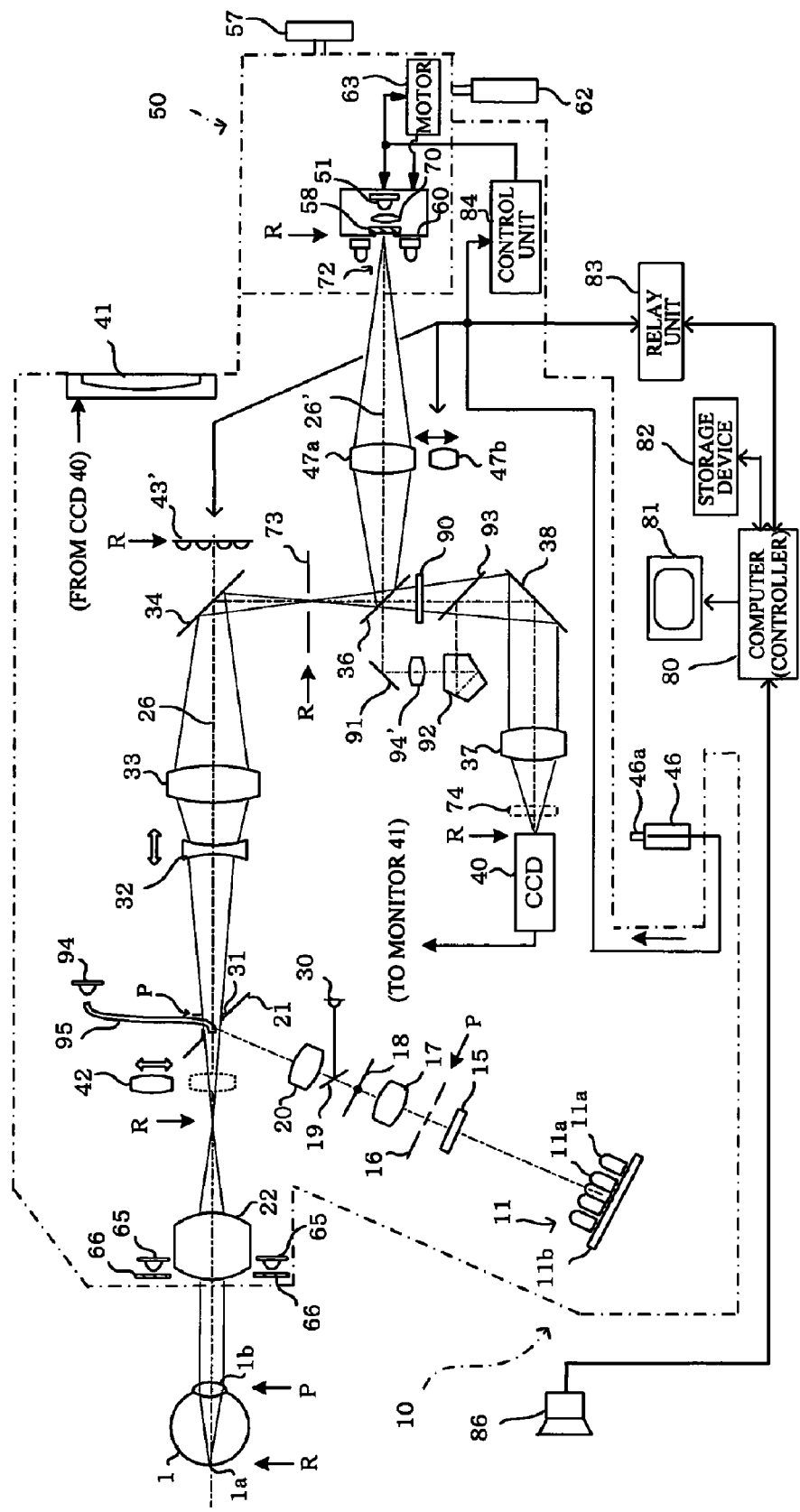
FIG. 4 is a schematic view showing the overall configuration of an ocular light stimulus apparatus according to a second embodiment of the present invention.

FIG. 4 shows a second embodiment of the present invention in which the background light source is disposed inside the stimulus light source unit, and the background light from the background light source is projected onto the ocular fundus via the observation/projection optical system. The same reference symbols are assigned to the same portions as FIG. 1 and a detailed description thereof is omitted.

In this embodiment, a background light source 72 for emitting background light is disposed inside the stimulus light source unit 50. An internal fixation lamp 43' composed of visible light light-emitting diodes is provided in the ocular fundus conjugate position in place of the liquid crystal plate 43, which functions as a fixation marker 43c.

Figure 5:
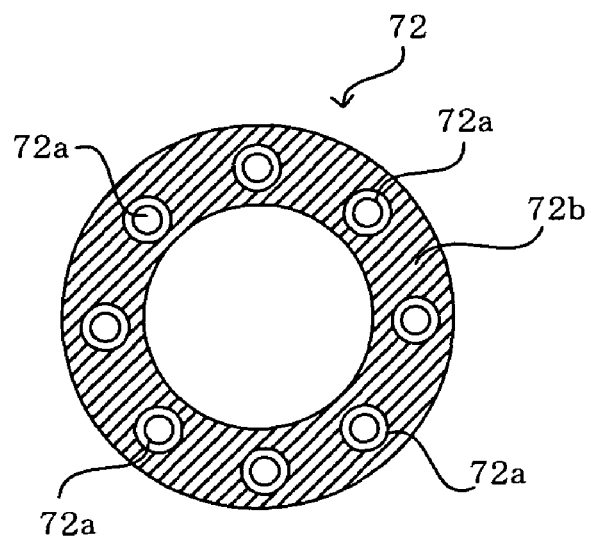
FIG. 5 is an illustrative view showing a background light source in the second embodiment.

The background light source 72 is composed of visible light light-emitting diodes 72a arranged in equidistant intervals about the periphery of a ring plate 72b, as shown in FIG. 5, and the center of the ring plate 72b is mounted on the casing of the stimulus light source unit 50 in alignment with the projection optical axis 26' so that the rotation of the indicator disc 60 is not obstructed. At this point, the background light source 72 is mounted so as to move within the xy plane vertical to the projection optical axis 26' together with the movement of the stimulus light source 51 using the lever 57.

Figure 6A:
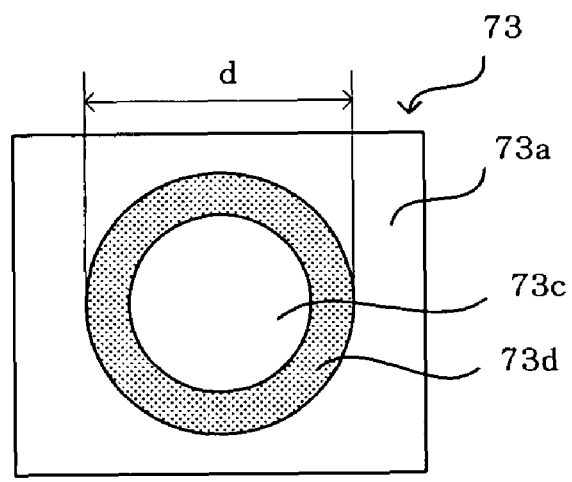
FIG. 6a is a plan view of a field stop used in the second embodiment.
Figure 6B:
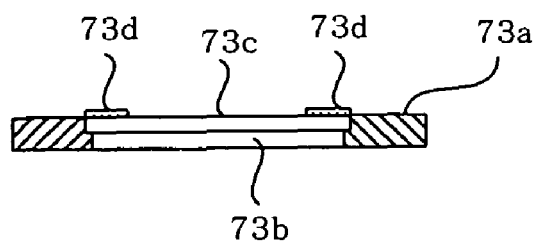
FIG. 6b is a cross-sectional view of the field stop used in the second embodiment.

In the second embodiment, a field stop 73 corresponding to the field stop 35 of the first embodiment has a circular cavity part 73b formed in a rectangular shade plate 73a, as shown in FIGS. 6a and 6b. A transparent glass plate 73c having diameter d is fitted into the cavity part 73b to provide an aperture stop. An infrared-cutting visible light-transmitting film 73d is vapor-deposited onto the external peripheral part of the glass plate 73c. The field stop 73 thus fabricated is disposed in the position R conjugate with the ocular fundus so that the center thereof is aligned with the observation optical axis 26.

In a local ERG examination in FIG. 4, the background light is projected from the background light source 72, passes through the magnification lens 47a, and is reflected by the half mirrors 36, 34. The background light reflected by the half mirror 34 is incident on the anterior ocular segment 1b of the examinee's eye via the imaging lens 33, the focus lens 32, the photographic stop 31, and the objective lens 22 and then projected onto the ocular fundus 1a in the same manner as the first embodiment.

With the configuration of FIG. 4 as well, the background light is projected onto the ocular fundus via the photographic stop 31. Therefore, the entire ocular fundus is uniformly illuminated, and the effect of scattered stimulus light is canceled out, ensuring an accurate local ERG examination. Also, the amount of the background light and the stimulus light can be kept constant regardless of the pupil diameter, and a highly reliable local ERG examination can be carried out with the same effects as the first embodiment.

In the second embodiment, since the background light passes through the field stop 73, the effective aperture diameter d (FIG. 6a) thereof can be made greater than the field stop 35 of the first embodiment 1 in order to increase the illumination range of the background light. However, when the aperture diameter of the field stop is increased, the infrared observation light from the ocular fundus enters into the image-capturing device 40 as stray light during ocular fundus observation, and is liable to interfere with the ocular fundus observation. Therefore, the infrared-cutting visible light-transmitting film 73d is formed on the peripheral part of the aperture of the field stop 73, as shown in FIGS. 6a and 6b. The background light from the background light source 72 can be transmitted toward the ocular fundus and directed to the ocular fundus in a wide range, while the infrared light that enters from the ocular fundus is blocked and the stray light that enters into the image-capturing device 40 is reduced by the vapor deposition film 73d.

In the second embodiment, the background light from the background light source 72 is visible light which passes through the half mirror 36 and enters into the image-capturing device 40 via the mirror 91, the lens 94', the prism 92, the half mirror 93, the mirror 38, and the lens 37. Therefore, an advantage is obtained in that the background light can be observed using the monitor 41. In this case, the sensitivity of the image-capturing device 40 is made to be high in the infrared region and low in the visible light region in order to prevent the background light from interfering with ocular fundus observation. Alternatively, a filter 74 that reduces visible light may be disposed in front of the image-capturing device 40 as shown by the chain line in FIG. 4.

The background light source 72 is disposed in an offset fashion from the ocular fundus conjugate position R in order to allow the background light to be diffused and projected onto the ocular fundus. Furthermore, a ring-shaped diffusion plate (not shown) may be disposed in front of the background light source 72 in order to increase the diffusion properties.

Figure 7:
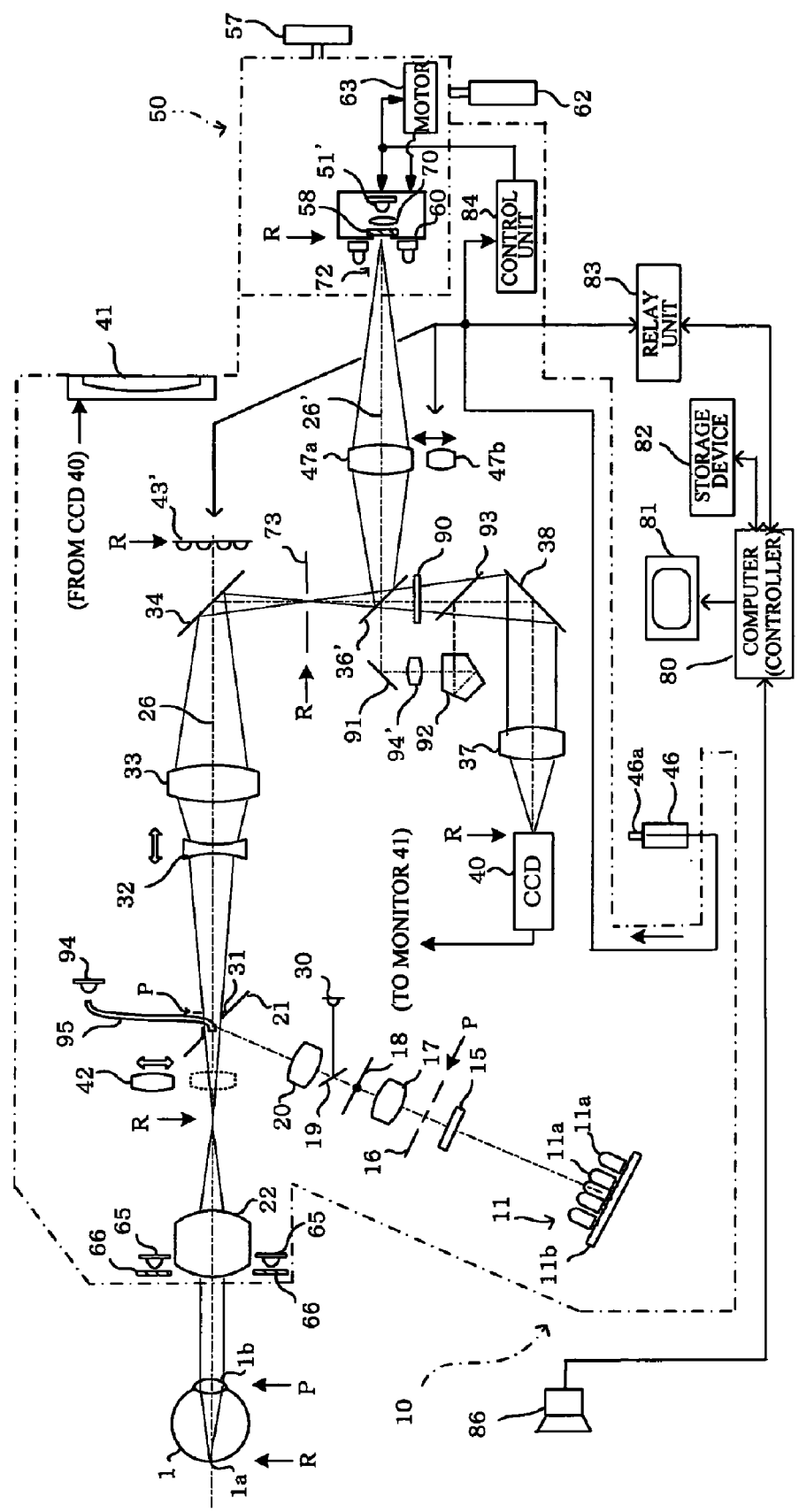
FIG. 7 is a schematic view showing the overall configuration of an ocular light stimulus apparatus according to a third embodiment of the present invention.

With the configuration of the second embodiment, there is an advantage in that the background light from the background light source 72 passes through the half mirror 36 and enters into the image-capturing device 40, and the background light can be observed on the monitor 41. On the other hand, there is a drawback in that the background light interferes with ocular fundus observation. In view of this fact, a third embodiment is proposed as shown in FIG. 7 in which the background light from the background light source 72 is prevented from entering into the image-capturing device 40. In FIG. 7, the same reference symbols are used for the same portions as those in FIGS. 1 and 4, and a detailed description thereof is omitted.

Figure 8:
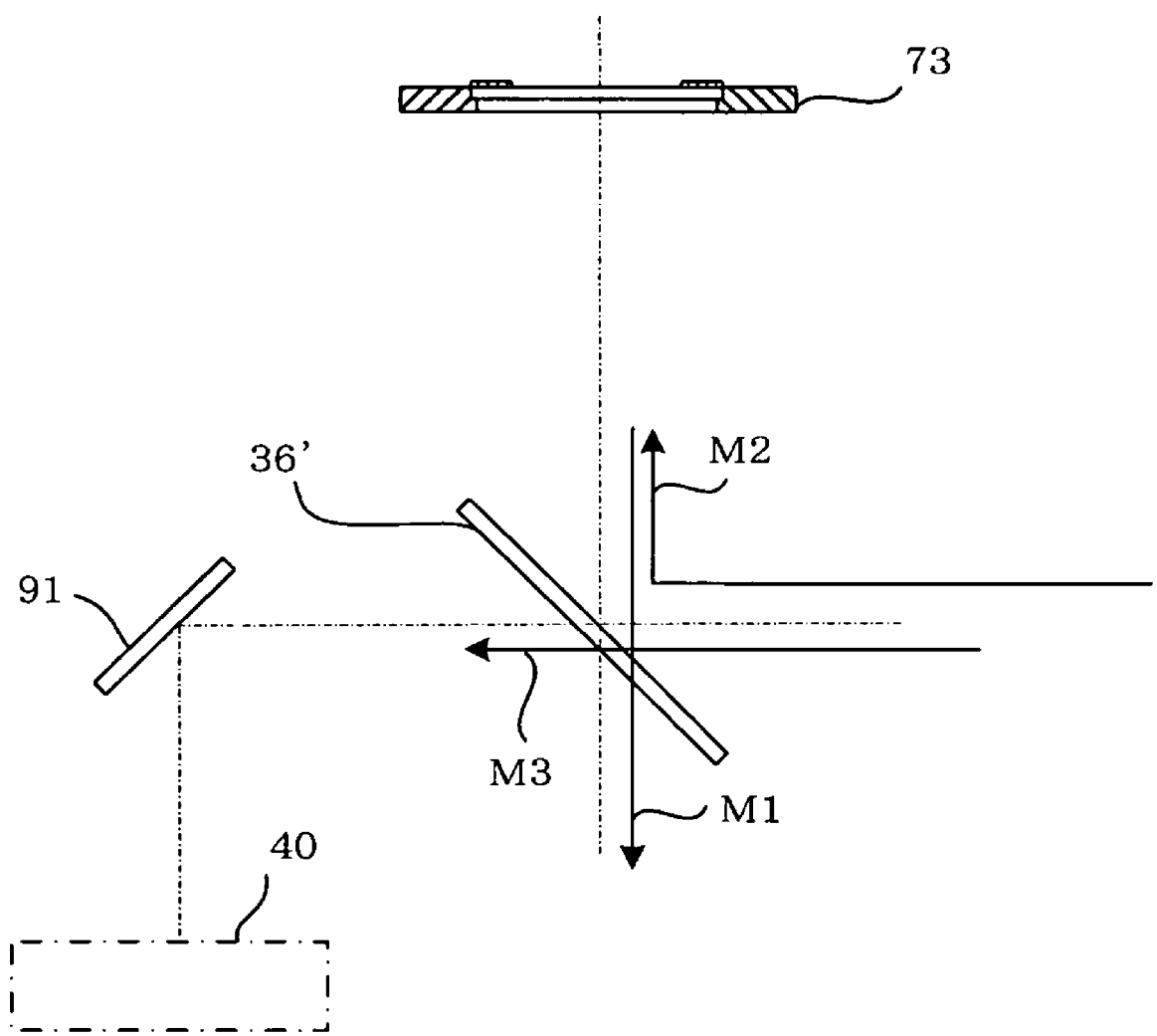
FIG. 8 is an illustrative view showing the reflection and transmission of a dichroic mirror used in the third embodiment.

In the third embodiment, a dichroic mirror 36' for reflecting visible light and transmitting infrared light is used as shown in FIG. 8 in place of the half mirror 36 of FIGS. 1 and 4. The ocular fundus image that passes through the field stop 73, the light of the WD light source 94 reflected from the examinee's eye, and the light of the FD light source 30 reflected therefrom are all infrared light. Therefore, the infrared light passes through the dichroic mirror 36' and enters into the image-capturing device 40, as indicated by M1 in FIG. 8. The visible light from the background light source 72 and the stimulus light source are reflected by the dichroic mirror 36', pass through the field stop 73, and are projected onto the ocular fundus, as indicated by M2. The reflection and transmission characteristics are the same as the half mirror 36 of FIGS. 1 and 4. However, since the dichroic mirror 36' does not transmit visible light, the visible light from the background light source 72 does not pass through the dichroic mirror 36' and enter into the image-capturing device 40, and the drawback in which the background light interferes with ocular fundus observation can be eliminated.

Since the stimulus light from the stimulus light source is also visible light, the stimulus light does not pass through the dichroic mirror 36' and does not enter into the image-capturing device 40. Therefore, the examiner cannot observe the irradiation position of the marker (stimulus light) and the size thereof via the monitor 41. Therefore, the stimulus light source 51' is used for emitting visible light and infrared light in the configuration of FIG. 7. The infrared component of the stimulus light therefore passes through the dichroic mirror 36' and enters the image-capturing device 40, as indicated by M3 in FIG. 8. In the same manner as the configuration in FIGS. 1 and 4, the irradiation position of the stimulus light and the size thereof can be observed via the monitor 41. The visible component of the stimulus light is reflected by the dichroic mirror 36' and directed to the ocular fundus as described above.

Figure 9:
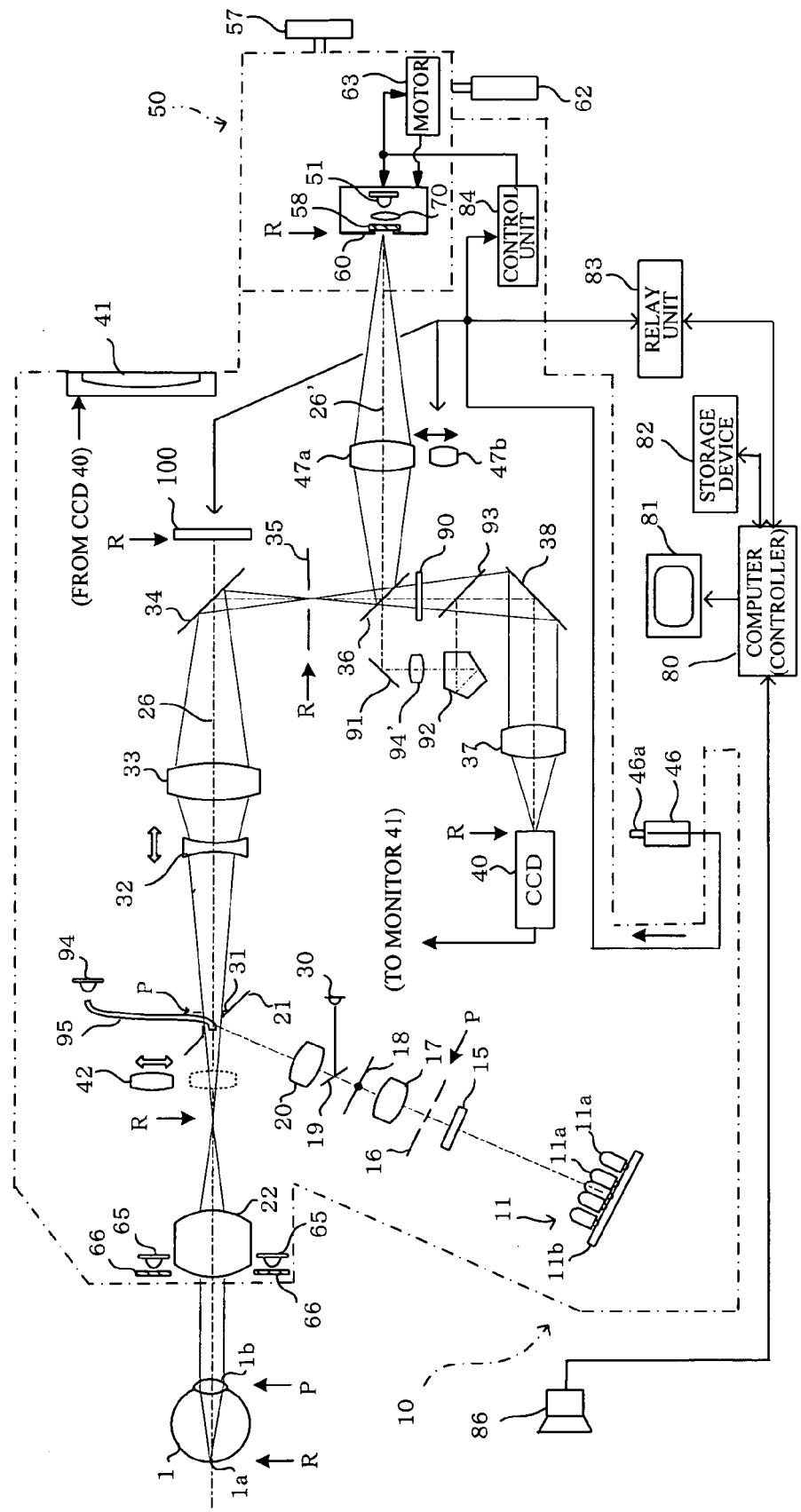
FIG. 9 is a schematic view showing the overall configuration of an ocular light stimulus apparatus according to a fourth embodiment of the present invention.

FIG. 9 shows a fourth embodiment in which a light-emitting panel 100 having a plurality of visible light-emitting diodes 100a is arranged as the background light source in the ocular fundus conjugate position in place of the liquid crystal panel 43 in the configuration of FIG. 1. In FIG. 9, the same reference symbols are assigned to the same portions as FIG. 1 and a detailed description thereof is omitted.

Figure 10:
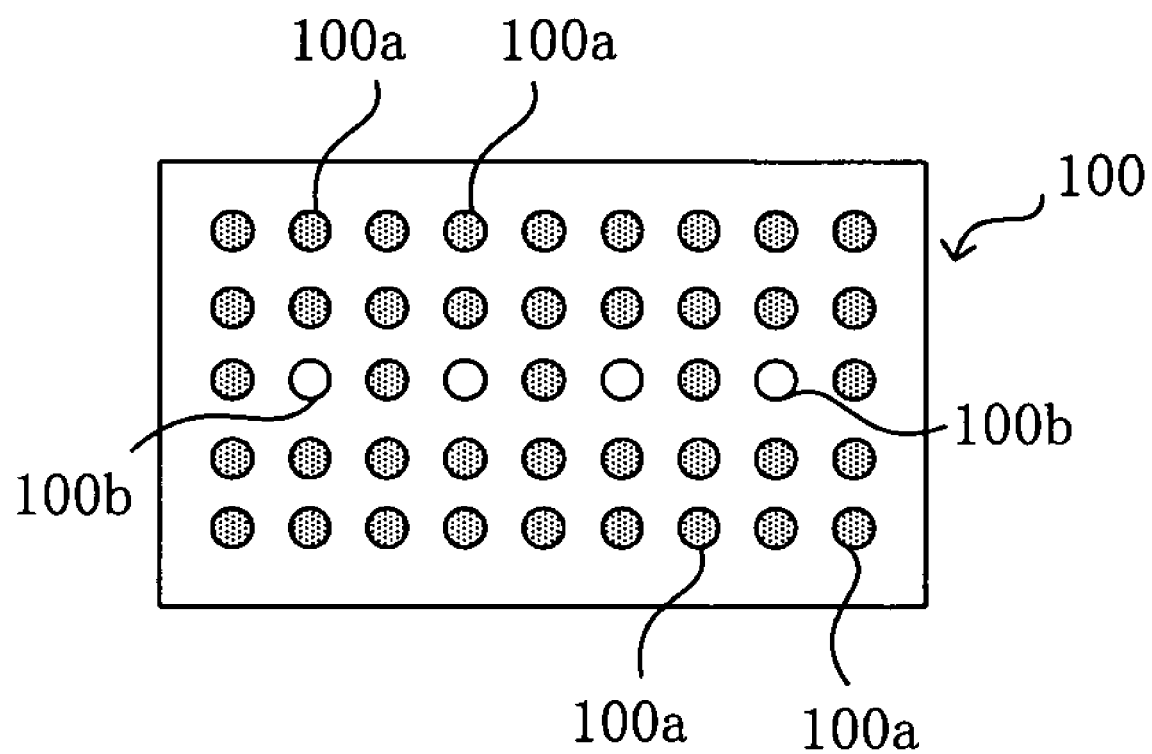
FIG. 10 is an illustrative view showing a light-emitting panel as a background light source used in the fourth embodiment.

As shown in FIG. 10, the light-emitting panel 100 is a panel in which visible light-emitting diodes are arranged vertically and horizontally at equidistant intervals. The light-emitting diodes 100a shown as dotted spots in the drawing are used as the background light source, and the light-emitting diodes 100b shown as white dots are used as fixation lamps. The center of the light-emitting panel 100 is disposed in the ocular fundus conjugate position behind the half mirror 34 in alignment with the optical axis 26.

The turning-on of the light-emitting diodes 100a occurs in synchronization with the movement of the stimulus light source 51 and is controlled by the computer 80. Since the stimulus light source 51 is moved in the xy plane vertical to the projection optical axis 26' using the lever 57, the position of the lever 57 is detected by a sensor (not shown) and the position of the lever is inputted to the computer 80. The computer 80 turns on one or a plurality of light-emitting diodes 100a in the vicinity of the xy position that corresponds to the xy coordinate in accordance with the position of the lever 57, i.e., the xy coordinate of the stimulus light source 51 in the xy plane. Such an arrangement provides a linking mechanism for moving the background light source together with the movement of the stimulus light source, and allows the illumination region of the background light to be set about the position onto which the stimulus light is projected. It is therefore possible to perform a local ERG examination with greater reliability.

Even when the background light source is not linked to the movement of the stimulus light source, the irradiation of the ocular fundus by background light is sufficiently effective as described above with reference to FIG. 1. Therefore, a switch (not shown) may be provided to the computer 80 so that it is possible to switch between a linked state in which the linking mechanism is enabled and an unlinked state in which the linking mechanism is disabled. In the case that the unlinked state is established, the computer 80 turns on one or a plurality of light-emitting diodes 100a positioned in the vicinity of the center of the light-emitting panel 100.

The light-emitting diodes 100a may be divided into two groups. The light-emitting diodes (first light source) that belong to one group are configured so as to be linked to the movement of the stimulus light source (i.e., the light-emitting diodes are turned on in accordance with the position of the stimulus light source 51), and the light-emitting diodes (second light source) that belong to the other group may be configured so that the diodes are fixed in turning-on position (i.e., are not turned on in accordance with the position of the stimulus light source 51).

When the alignment and focus operations are performed, any of the light-emitting diodes 100b are turned on, and the examiner can reliably perform the alignment and focus operations by having the examinee gaze at the activated light-emitting diode.

At this point, it is preferred that the position of the stimulus light and/or the background light on the ocular fundus be changed depending on the fixation position. Therefore, the linking/unlinking between the background light source and the stimulus light source may be automatically switched in accordance with the position of the internal fixation lamp.

Also, the linking/unlinking between the background light source and the stimulus light source may be automatically switched in accordance with the position of the stimulus light or the size thereof.

What is claimed is:

1. An ocular light stimulus apparatus in which the ocular fundus of an examinee's eye is irradiated with ocular fundus observation light to observe the ocular fundus and is irradiated with background light and stimulus light to locally stimulate the retina with the stimulus light and perform a biological examination using a bioelectrical signal obtained from the retina, the ocular light stimulus apparatus comprising:
   a ring slit disposed in a position substantially conjugate with the anterior ocular segment of the eye to be examined so that the ocular fundus of the eye to be examined is irradiated with the ocular fundus observation light via the ring slit; and
   a photographic stop disposed in a position substantially conjugate with the anterior ocular segment of the eye to be examined so that the ocular fundus of the eye to be examined is irradiated with the stimulus light and the background light via the photographic stop.

2. An ocular light stimulus apparatus according to claim 1; further comprising a background light source for emitting the background light, the background light source serving as an internal fixation lamp for fixating the position of the eye to be.

3. An ocular light stimulus apparatus according to claim 2; wherein the background light source comprises a panel for emitting visible light when a voltage is applied to the panel to display a marker having a color that is different from that of the background light, the marker being used as the internal fixation lamp.

4. An ocular light stimulus apparatus according to claim 1; further comprising a background light source for emitting the background light and a stimulus light source for emitting the stimulus light, the background light source and the stimulus light source being mounted on a common unit so that the background light source undergoes movement with movement of the stimulus light source.

5. An ocular light stimulus apparatus according to claim 4; wherein the stimulus light source includes a visible light component for stimulating the eye to be examined and an infrared light component for observing the position of the stimulus light.

6. An ocular light stimulus apparatus according to claim 4; further comprising a linking mechanism for linking movement of the background light source with movement of the stimulus light source, the linking mechanism being configured to be switched between a linked state in which the linking mechanism is enabled and an unlinked state in which the linking mechanism is disabled.

7. An ocular light stimulus apparatus according to claim 6; wherein the background light source comprises first and second light sources, the first light source being configured so as to be turned on in accordance with a position of the stimulus light source, and the second light source being configured so as to not be turned on in accordance with the position of the stimulus light source.

8. An ocular light stimulus apparatus according to claim 6; wherein the switching between linking/unlinking of the linking mechanism is automatically performed in accordance with the position of the background light source, a position of the stimulus light or the size of the stimulus light.

9. An ocular light stimulus apparatus according to claim 1; further comprising a field stop having a ring-shaped, infrared-blocking visible light-transmitting portion for blocking infrared light from the ocular fundus and transmitting visible background light toward the ocular fundus.

10. An ocular light stimulus apparatus according to claim 1; further comprising an illumination optical system containing the ring slit and a photographic optical system containing the photographic stop.

11. An ocular light stimulus apparatus for providing the ocular fundus of an examinee's eye under examination with observation light to observe the ocular fundus and providing localized background light and stimulus light to a retina of the ocular fundus to perform biological examination through use of a bioelectrical signal from the retina, the ocular light stimulus apparatus comprising:
 a ring slit disposed in a position substantially conjugate with the anterior ocular segment of the eye to be examined;
 a first light irradiating device for irradiating the ocular fundus of the eye with the observation light via the ring slit;
 a photographic stop disposed in a position substantially conjugate with the anterior ocular segment of the eye; and
 a second light irradiating device for irradiating the ocular fundus of the eye with the stimulus light and the background light via the photographic stop.

12. An ocular light stimulus apparatus according to claim 11; wherein each of the first and second light irradiating devices comprises at least one light-emitting diode.

13. An ocular light stimulus apparatus according to claim 11; wherein the second light irradiating device comprises a background light source for emitting the background light and a stimulus light source for emitting the stimulus light, the background light source and the stimulus light source being mounted on a common unit so that the background light source undergoes movement with movement of the stimulus light source.

14. An ocular light stimulus apparatus according to claim 13; wherein the stimulus light source includes a visible light component for stimulating the eye to be examined and an infrared light component for observing the position of the stimulus light.

15. An ocular light stimulus apparatus according to claim 11; further comprising a field stop having a ring-shaped, infrared-blocking visible light-transmitting portion for blocking infrared light from the ocular fundus and transmitting visible background light toward the ocular fundus.

* * * * *